United States Patent [19]

Ohlendorf et al.

[11] Patent Number: 4,828,765
[45] Date of Patent: May 9, 1989

[54] OXYALKYLATED QUATERNARY AMMONIUM COMPOUNDS AND THEIR USE AS DRAG REDUCING AGENTS

[75] Inventors: Dieter Ohlendorf, Liederbach; Manfred Hofinger, Burgkirchen, Fed. Rep. of Germany

[73] Assignee: Hoechst Aktiengesellschaft, Frankfurt am Main, Fed. Rep. of Germany

[21] Appl. No.: 151,404

[22] Filed: Feb. 2, 1988

Related U.S. Application Data

[63] Continuation of Ser. No. 681,301, Dec. 13, 1984, abandoned.

[30] Foreign Application Priority Data

Dec. 17, 1983 [DE] Fed. Rep. of Germany ....... 3345806

[51] Int. Cl.⁴ .............................................. C07C 87/30
[52] U.S. Cl. .................................................. 260/501.15
[58] Field of Search ............... 260/501.15; 252/8.55 R

[56] References Cited

U.S. PATENT DOCUMENTS 2,812,350 11/1957 Niedehauser ................... 260/501.15
3,328,464 6/1967 Gündel et al. ................ 260/501.15

OTHER PUBLICATIONS

*Chemical Abstracts,* vol. 101, No. 132976m, 6/28/84, Geke et al., "Regeneration or Recycling of Aqueous Degreasing and Cleaning Solutions".
*Chemical Abstracts,* vol. 101, No. 193,175, 6/11/84, Nikka et al., "Antistatic Agent Compositions".
Schönfeldt, *Surface Active Ethylene Oxide Adducts,* 1969, pp. 671–672, 676.
*Chemical Abstracts,* vol. 101, No. 198625c, 1984, Molliaris et al., "Micellar Properties of Quanternary Ammonium Functional Groups on Their Ionic Heads".

Primary Examiner—Richard L. Raymond
Assistant Examiner—Raymond Covington

[57] ABSTRACT

Quaternary ammonium compounds of the formula

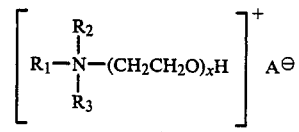

in which $R_1$ denotes an alkyl or alkenyl radical with 12 to 22 carbon atoms; $R_2$ and $R_3$ are identical or different and denote an alkyl radical with 1 to 4 carbon atoms; x denotes an integral or non-integral number from 1 to 3; and $A^\ominus$ denotes an alkyl- or alkenyl-sulfonate anion, an alkyl or alkenyl-carbonate anion or a benzoate, naphthoate or phenylsulfonate anion, the tosylate ion being excluded, a process for their preparation and their use as drag reducing agents in liquids with turbulent flow.

7 Claims, 1 Drawing Sheet

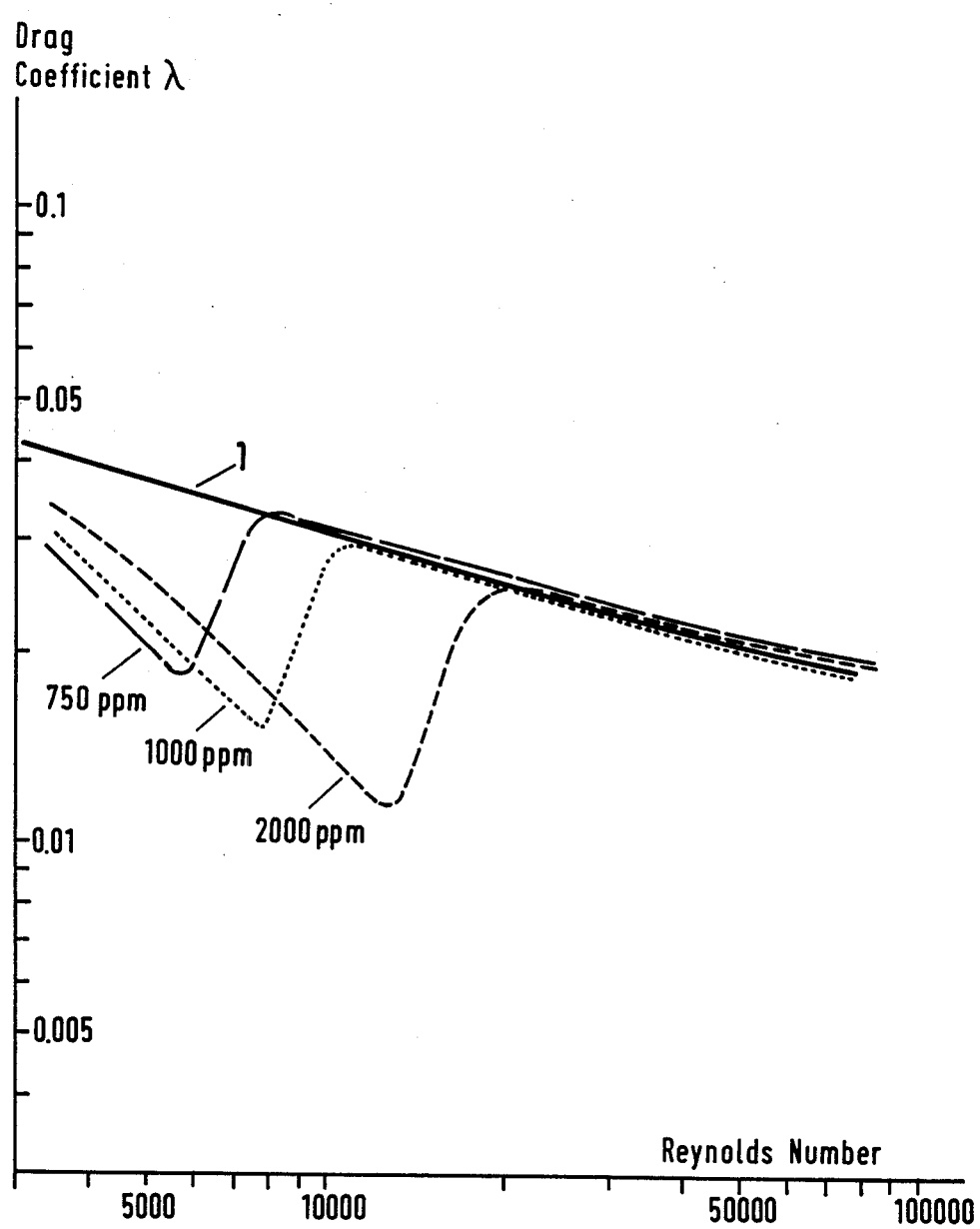

OXYALKYLATED QUATERNARY AMMONIUM COMPOUNDS AND THEIR USE AS DRAG REDUCING AGENTS

This application is a continuation of our copending application Ser. No. 681,301, filed Dec. 13, 1984 now abandoned.

It is generally known that liquids with turbulent flow experience a frictional drag on the adjacent walls. It is also known that this frictional drag can be reduced by addition of small amounts of certain substances. Substances which display this action are called drag reducing agents (abbreviated to DRA below). A drag reducing agent is therefore understood as meaning a substance which, when added in a relatively small amount to a liquid with turbulent or pulsating flow, allows this liquid to flow more rapidly - under otherwise identical conditions. Drag reducing agents mean that more liquid can be conveyed with a given pump through a given pipeline.

In many cases, this fact alone is already a technical advantage, if, for example, a pipeline is loaded to full capacity in normal operation and a peak consumption needed to be conveyed at certain times. Since more liquid can be conveyed with a given pump output by using drag reducing agents, the associated saving in energy will also be an industrial advantage in many cases. Finally, if it is not the intention to increase the throughput, the pressure loss can be reduced or pipelines of smaller cross-section can be used by employing DRA. Both are measures which can improve the efficiency in operation of a pipeline.

Besides high molecular weight compounds, such as polyethylene oxide and polyacrylamide, solutions of some surfactants are known as drag reducing agents for water or aqueous solutions. However, the addition of high molecular weight compounds as drag reducing agents is only of limited practical applicability, since they irreversibly lose their effectiveness as drag reducing agents in regions of high shear and tensile stress, such as, for example, in pumps or to a small degree in the turbulent boundary layer close to the wall of the tube, due to mechanical degradation. High molecular weight additives are consequently unsuitable for closed water circulations in which the same aqueous solution is continuously pumped around a pipeline system, since the irreversible mechanical degradation necessitates continuous topping up with effective high molecular weight substance.

Additives comprising surfactants in water are known not to have the disadvantage of irreversible mechanical degradation (U.S. Pat. No. 3,961,639). Although mechanical degradation can also be observed here in regions of very high tensile and sheer stress, such as, for example, in pumps, this is completely reversible as soon as the solution has passed these regions. Thus, the drag reducing action of an aqueous solution of Na oleate on addition of KCl+KOH or NaCl+NaOH is reported by Savins (Reol. Acta 6, 323 (1967)). Asslanow et al. Akad. Nauk. SSSr, Mekh. Zhidk. Gaza 1, 36–43 (1980) investigated, inter alia, aqueous solutions of Na laurate, myristate, palmitate and stearate a pH 11 as DRA.

Chang et al. (U.S. Pat. No. 3,961,639) described the drag reducing action of aqueous solutions of some nonionic surfactants with an added foreign electrolyte at temperatures in the region of the turbidity point.

Considerable disadvantages of the surfactant solutions mentioned are their relatively high use concentrations of at least 0.25% by weight, the formation of insoluble soaps with $Ca^{2+}$ and other cations, the formation of two phases which separate on prolonged standing and can lead to blockages, the necessity of the addition of corrosion promoting foreign electrolytes, and a very narrow temperature range of a few degrees celsius in which the DR action occurs. It is also known that aqueous solutions of some cationic surfactants, such as, for example, cetylpyridinium bromide (Inzh. Fizh. Zh. 38, No. 6, 1031-1037 (1980)) or cetyltrimethylammonium bromide (Nature 214, 585–586 (1967)), in each case in a 1:1 molar mixture with α-naphthol, are effective DRA.

However, such mixtures lose their effectiveness as DRA within a few days due to chemical degradation (U.S. Pat. No. 3,961,639; J. L. Jakin, J. L. Chang S. DI-1 to DI-14 Conference Proceeding: Intern. Conference on Drag Reduction, 4.-6.9.1974 Rolla Missouri, U.S.A.). The poor water-solubility of the α-naphthol and, in particular, the very high content of corrosive halide ions, such as, for example, $Br^-$, are further decisive disadvantages of these mixtures. The use of n-hexadecyltrimethylammoniumsalicylate as a DRA is also known. However, this compound can be prepared in a form in which it is free from corrosive halogen ions only by expensive purification operations, and also has an activity as a DRA only up to a temperature of 70° C. The use of various quaternary ammonium compounds as DRA is also known from the Application WO 83/01583.

Surprisingly, it has now been found that, in contrast to all the other surfactants hitherto known as DRA, the compounds shown below are active, in the pure form even without any additives in aqueous solution and already at very small concentrations, as drag reducing agents, these surfactants being completely free from corrosive electrolytes, such as, for example, $Cl^-$ or $Br^-$, because of their preparation process. It has furthermore been found that these compounds do not lose their effectiveness even on continuous exposure to stress for weeks. In addition, some of the compounds are also effective above 80° C.

The invention relates to novel quaternary ammonium compounds of the formula

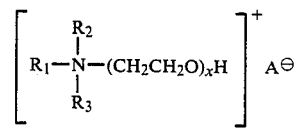

in which $R_1$ denotes an alkyl or alkenyl radical with 12 to 22 carbon atoms; $R_2$ and $R_3$ are identical or different and denote an alkyl radical with 1 to 4 carbon atoms; X denotes an integral or non-integral number from 1 to 3; and $A^\ominus$ denotes an alkyl- or alkenyl-sulfonate anion, preferably a straight-chain $C_6$-$C_9$-alkylsulfonate or $C_6$-$C_9$-alkenyl-sulfonate anion, wherein the sum of the carbon atoms in $R_1$ and in the sulfonate anion should be at least 21, an alkyl- or alkenyl-carboxylate anion, preferably a straight-chain $C_6$-$C_9$-alkylcarbonate or $C_6$-$C_9$-alkenylcarbonate anion, wherein the sum of the carbon atoms in $R_1$ and in the carboxylate anion should be at least 23, or a benzoate, naphthoate or phenylsulfonate anion, preferably an anion of the formulae

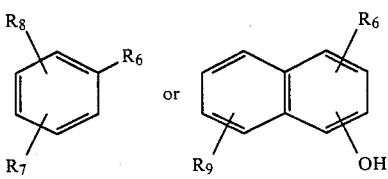

in which $R_6$ is $-COO^-$ or $-SO_3^-$, $R_7$ is hydrogen or hydroxyl in position 2 or 3 relative to $R_6$, or $NO_2$, fluorine, chlorine, bromine or iodine in position 3 relative $R_6$, $R_8$ is $C_1-C_5$-alkyl, $C_2-C_5$-alkenyl or $C_1-C_5$-alkoxy in position 3, 4 or 5 relative to $R_6$, and $R_9$ is hydrogen or methyl, the tosylate ion being excluded.

Particularly preferred cations are those of the formula

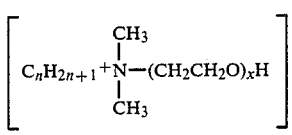

in which X is an integral or non-integral number from 1 to 1.5 and n is a number from 12 to 24, in combination with the following anions
  (a) with $C_6H_{13}SO_3^-$ for n=20-24
  (b) with $C_7H_{15}SO_3^-$ for n=14-22
  (c) with $C_8H_{17}SO_3^-$ for n=14-20
  (d) with 2-phenylsulfonate, m-halogenobenzoate or salicylate
  (e) with an anion of the formula

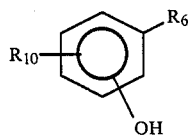

where $R_6=SO_3^-$ or $COO^-$ and $R_{10}=C_1-C_4$ alkyl or $C_1-C_4$-alkoxy, preferably in position 4 or 5 relative to $R_6$, and with OH preferably in position 2 or 3 relative to the carboxyl group.
  (f) with the anions 2-hydroxy-1-naphthoate, 3-(or 4)-hydroxy-2-naphthoate or the corresponding derivatives of naphtholsulfonic acids and
  (g) with $C_7H_{15}COO^-$ for n=16-24 with $C_8H_{17}COO^-$ for n=16-24 with $C_9H_{19}COO^-$ for n=14-22 with $C_{10}H_{27}COO^-$ for n=14-16

The ammonium compounds according to the invention are prepared starting from tertiary amines of the formula

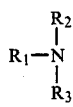

These can in turn be obtained in a known manner by reductive alkylation of primary amines with formaldehyde. The classical reaction procedure here is the Leuckart-Wallach reaction, using formic acid as the reducing agent. In more modern processes, the reductive alkylation with formaldehyde is carried out in the presence of nickel catalysts under hydrogen pressure. Additional possibilities for the preparation of these unsymmetric tertiary amines are the reaction of fatty alcohols with dimethylamine in the presence of copper catalysts, chromium catalysts or cobalt catalysts, and the reactions of fatty nitriles, alkyl halides, alkanals or fatty acids with dimethylamine.

The tertiary amine is now reacted with the acid component and with ethylene oxide. These two reactants can be added and reacted simultaneously. However, it is preferable first to carry out the neutralization with the particular acid, which can be effected during the heating up to the reaction temperature, and then to add the ethylene oxide. An equimolar amount of the carboxylic acid, based on the tertiary amine, is employed, and the amount of ethylene oxide is 1.5 to 5 moles, preferably about 2 moles, per mole of amine. The reaction is carried out in an aqueous medium, to which a polar organic solvent, for example an alkanol with a low number of carbon atoms, can be added if appropriate. The reaction is carried out in a closed reaction vessel at a temperature of 80° to 90° C. under a slightly increased pressure of up to 3 bar. The reaction time is in general 3-7 hours.

The quaternary ammonium compounds thus obtained, including the compounds in which $A^\ominus$ denotes a tosylate ion, are suitable for reducing the frictional drag of aqueous media. They are added in concentrations of 0.05 to 5% by weight, preferably 0.1 to 1% by weight and particularly preferably 0.2 to 0.5% by weight; however, a different lower critical concentration limit for adequate effectiveness as DRA exists for each surfactant, and this can be determined by a simple preliminary experiment, as described below. The effect as a DRA also depends on the temperature. The compounds claimed according to the invention exhibit an adequate action as DRA distributed over the temperature range from 0° C. to 120° C., each individual surfactant having a particular range of action over about 40° C. (±10° C.). The lower temperature limit for all the surfactants is in each case the solubility temperature in water (Krafft point). However, if the surfactant is in solution, the temperature can fall below the solubility temperature by 5° to 20° C. for a few hours to weeks. If the $C_{12}$-alkyl compounds are used, the surfactants mentioned are also suitable as DRA for temperatures below 0° C., if the melting point of the solvent water is reduced by admixing other solvents, such as, for example, ethylene glycol or isopropanol. Reduction of the melting point by addition of electrolytes without loss in the effectiveness as a DRA is possible to only a limited degree. The following compounds are particularly suitable for temperatures in the range from 80° to 120° C.:

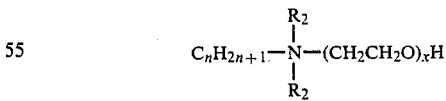

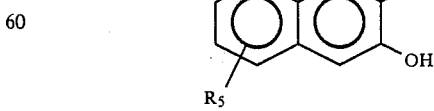

in which n is an integer from 20 to 24, x is an integral or non-integral number from 1 to 1.5, $R_2$ represents methyl or ethyl, $R_3$ represents $COO^-$ or $SO_3^-$ and $R_5$ represents H or methyl.

It has furthermore been found that by increasing the pH of the aqueous solution to values above 9, preferably to pH 9.5 to 11, by adding NaOH or other bases or by adding $Na_2CO_3$ or other salts which increase the pH value, the effectiveness as a DRA is either uninfluenced, as, for example, with the sulfonates, or is substantially improved, as, for example, with the hydroxybenzoates and the compounds derived therefrom. A reduction of the pH to values below 4.5 with HCL or other strong acids leads to the same influencing of the DR action of the surfactants.

The addition of other foreign eletrolytes leads to no influencing, such as, for example, in the case of the sulfonates, to an improvement of the effect as DRA, as, for example, in the case of the hydroxybenzoates and the compounds derived therefrom.

Examples of possible foreign electrolytes of this type are weak acids, such as acetic acid or formic acid, and salts formed from the following ions: alkali metal, alkaline earth metal, transition metal, ammonium or ammonium cations; and halides, $ClO_3^\ominus$, $ClO_4^\ominus$, $BrO_3^\ominus$, $JO_3^{2\ominus}$, $S_2O_3^{2\ominus}$, $SO_4^{2\ominus}$, $S_2O_8^{2\ominus}$, $NO_2^\ominus$, $B_4O_7^{2\ominus}$, $NO_3^\ominus$, $PO_4^{3\ominus}$, $CO_3^{2\ominus}$, $CH_3COO^\ominus$, $C_2O_4^{2\ominus}$, $CN^\ominus$, $CrO_4^{2\ominus}$ or $Cr_2O_7^{2\ominus}$. The upper limit of the amount of these foreign electrolytes which can be added to the aqueous surfactant solution is determined by the concentration at which a salting out effect for the surfactant occurs, together with a decrease in or the complete disappearance of the effectiveness as a DRA.

The effect of the foreign eletrolytes also depends on the valency of the ions, and in particular the effect shifts in the direction of lower concentrations according to the following scheme: 1-1-valent electrolyte 2-1-valent electrolyte 1-2-valent electrolyte 2-2-valent electrolyte 3-2-valent electrolyte 2-3-valent electrolyte. The improvement in the activity as drag reducing agents in the case of the hydroxybenzoates and the compounds derived therefrom is particularly effective when a salt which simultaneously increases the pH value to pH greater than 9.9 is added. Thus, for example, the addition of $Na_2CO_3$ in the concentration range from 0.1 C to 10 C, where C is the molar concentration of the surfactant employed, has a particularly positive result.

Instead of adding salts, it is also possible to follow a procedure in which the halogen salt of the cationic surfactant $R_1K^+Hal^-$, such as, for example, $[C_nH_{2n+1}N(CH_3)_2(CH_2CH_2O)_xH]$ Hal, where $x=1$ to 1.5 and where Hal=Cl, Br or I, in a molar ratio of 1:1 with an alkali metal salt of the anion NaA, such as, for example, Na-n-alkyl-1-sulfonate, Na hydroxybenzoate and the acid anion derived therefrom, or such as, for example, Na hydroxynaphthoate, is used as the drag reducing agent. The effect is then equivalent to the effect which is achieved with the pure surfactant salts with the addition of alkali metal halides. Mixtures which deviate from the molar ratio of 1:1, such as, for example, to 1:2, also display an effect as DRA.

The maximum activity as drag reducing agents also depends on the time which has elapsed since the preparation of the aqueous surfactant solution. Although the surfactant solutions already exhibit an action as drag reducing agents immediately after the solutions have been prepared, this action may further change considerably during one week. The time required to achieve optimum action can easily be determined for an individual case by simple experiments. In most cases, the optimum action is reached after one week. No further change or improvement in the action then occurs.

Some surfactants, such as, for example, hexadecylpyridiniumsalicylate are known (H. Hoffmann et al., Ber. Bunsenges. Phys. Chem. 85 (1981) 255) to build up large non-spherical, usually rod-shaped micelles from the individual surfactant ions and counter-ions from a quite particular concentration which is characteristic for each surfactant, the $CMC_{II}$.

Surprisingly, it has now been found that surfactants in aqueous solution are always effective as drag reducing agents if they form non-spherical, preferably rod-shaped micelles at concentrations greater than the $CMC_{II}$. Non-spherical, preferably rod-shaped, micelles exist if, on investigation of the surfactant solution with the aid of the electric birefringence method with a pulsed, rectangular electrical field (E. Frédericq and C. Houssier, Electric Dichroism and Electric Birefringence, Clarendon Press, Oxford 1073 and H. Hoffmann et al., Ber. Bunsenges. Phys. Chem. 85 (1981) 255), a measurement signal is found from which, from its decrease, a relaxation time of greater than 0.05 $\mu s$ can be determined.

The lower concentration limit from which a surfactant in aqueous solution is effective as a drag reducing agent is thus always determined by the $CMC_{II}$, preferably by 1.5 times the concentration value of the $CMC_{II}$. The $CMC_{II}$ can be determined, for example, by measuring the electrical conductivity of the surfactant solution as a function of the surfactant concentration, as described by H. Hoffmann et al. (Ber. Bunsenges. Phys. Chem. 85 (1981) 255). It has been found that the $CMC_{II}$ value depends on the temperature and shifts to higher surfactant concentrations as the temperature increases. Thus, for example, for $C_{16}DE$-Sal, the $CMC_{II}$ is 250 ppm at 40° C. and 2,000 ppm at 60° C.

Determination of the $CMC_{II}$ at the use temperature with the aid of electrical conductivity is a suitable preliminary experiment for establishing the minimum surfactant concentration necessary to achieve an adequate effect as a DRA in a particular temperature range.

In all the investigations mentioned, it has so far been found that only surfactants which contain cations of the following formulae

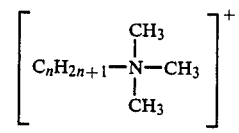

and

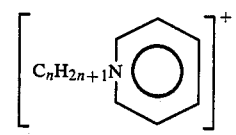

where n = 12-24 build up rod-shaped micelles and are effective as drag reducing agents. However, since even small variations on the quaternary nitrogen lead to a loss in effectiveness as a DRA, the action of the compounds claimed here, which contain an additional hydrophilic group, as DRA is completely unpredictable and surprising.

The surfactants mentioned are in most cases investigated for their effectiveness as DRA in the usual manner, by measuring the drop in pressure ($\Delta P$) over the distance L when the particular aqueous solution of the surfactants flows through a pipe of cross-section d at various flow rates u. The dimensional parameters of drag coefficient λ and Reynolds' number Re can be calculated from these values:

$$\lambda = \frac{2d}{\rho u^2} \cdot \frac{\Delta P}{L}$$

$$Re = \frac{ud}{\nu}$$

in which $\rho$ denotes the density and $\nu$ denotes the kinematic viscosity. For $\rho$ and $\nu$, the corresponding values for the pure solvent, water, are usually employed. The values λ and Re thus obtained for the surfactant solutions investigated have been compared in a customary double-logarithmic plot of $\nu$ against Re with the corresponding values for pure water, represented by $$1\sqrt{\lambda} = 2 \log Re \sqrt{\lambda} - 0.8$$

An effect as a DRA or a reduction in drag exists if: $\lambda_{H_2O} - \lambda_{SB} > 0$, and the degree of reduction in drag in percent can be calculated as follows:

$$\alpha = \% \text{ reduction in drag} = \frac{\lambda_{H_2O} - \lambda_{SB}}{\lambda_{H_2O}} \times 100$$

As can be seen from FIG. 1, the surfactant solutions mentioned act as DRA in a manner such that the percentage reduction in drag increases as the Reynolds' number increases, but then decreases again very rapidly after a certain Reynolds' number, $Re_{max}$, has been exceeded, with maximum percentage reduction in drag. The degree of effectiveness of a surfactant solution as a DRA is characterised in the following text by the size of $Re_{max}$; accordingly, a surfactant solution with $Re_{max} = 20,000$ is more effective as a DRA than a surfactant solution with $Re_{max} = 10,000$. The associated $\alpha$ value is characterised by $\alpha_{max}$. The investigations of the surfactant solutions in most cases only gave reproducible results when the aqueous solutions of the surfactant salts were each kept at the measurement temperatures for about 1 week before the measurements. Although the solutions also exhibit an action as drag reducing agents immediately after being prepared, this can further change significantly in the course of one week.

The surfactants thus treated were subjected to a large number of tests. Thus, long-term experiments over several days showed, as can be seen from Example 22, that no decrease in their drag-reducing action as a result of mechanical or chemical degradation occurs in the surfactants listed. It was furthermore found that the effectiveness of the surfactants mentioned as DRA increases as the concentration increases; however, the viscosity of the solutions also increases, so that the percentage reduction in drag decreases at smaller Reynolds' numbers, as can be seen from the drawing.

The investigations carried out show that the surfactant salts mentioned are suitable as drag reducing agents in all cases where water is pumped through pipelines, especially where water is continuously pumped round a pipline system in circulation, such as, for example, in cooling and heating circulations, since a high long-term stability of the DRA, as displayed by the surfactant salts mentioned, is absolutely necessary.

The surfactant salts can be metered into the water flowing through the pipelines either in the form of a concentrated surfactant solution (1–10% by weight) or by addition of the pure crystalline surfactant salts. Metering into the pipeline system shortly before a pump is the most advantageous site, because of the good mixing effect.

PREPARATION EXAMPLES:

Example 1

Hexadecyl-dimethyl-poly(oxyethyl)$_{1-2}$-ammonium salicylate 137 g (0.5 mole) of hexadecyldimethylamine, 69.1 g (0.5 mole) of salicylic acid, 166 g of water and 42 g of isopropanol are initially introduced into a 1 litre stirred autoclave. After a reaction temperature of 80° C. has been reached, 44 g (1.09 moles) of ethylene oxide are added such that a maximum pressure of 3 bar is reached and a temperature of 95° C. is not exceeded. The total reaction time is about 6–7 hours at about 80° C., the pressure falling to 0.2 bar. Analysis of this product shows a degree of quaternization of 95%.

The degree of quaternization is determined as the ratio from two-phase titration of the quaternary ammonium compound at pH 1 to 2 and pH 10 with sodium dodecylsulfate.

Example 2

Dodecyl-dimethyl-poly(oxyethyl)$_{1-2}$-ammonium salicylate

To prepare this compound, 130.1 g (0.6 mole) of dodecyldimethylamine and 82.9 g (0.6 mole) of salicylic acid in 200 g of water and 47 g of isopropanol are reacted with 52.9 g (1.2 moles) of ethylene oxide as described in Example 1. The degree of quaternization of the clear liquid formed is 98%.

Example 3

Eicosyl/docosyl-dimethyl-poly(oxyethyl)$_{1-2}$-ammonium salicylate

To prepare the substance mentioned, 175 g (0.5 mole) of eicosyl/docosyl-dimethylamine and 69.1 g (0.5 mole) of salicylic acid in 168 g of water and 150 g of isopropanol are reacted with 44 g (1.0 mole) of ethylene oxide as described in Example 1. The degree of quaternization of the product is 98.5%. It is advisable for most of the isopropanol initially introduced to be removed by azeotropic distillation with water.

Example 4

Hexadecyl-dimethyl-poly(oxyethyl)$_{1-2}$-ammonium caprylate

To prepare this compound, 137 g (0.5 mole) of hexadecyldimethylamine and 72.1 g (0.5 mole) of caprylic acid in 162 g of water and 40 g of isopropanol are reacted with 44 g (1.0 mole) of ethylene oxide as described in Example 1. The degree of quaternization is 91.5%.

Example 5

Hexadecyl-dimethyl-poly(oxyethyl)$_{1-2}$-ammonium (2-hydroxy-4-methoxy)benzoate This compound is obtained analogously to Example 1 by reacting 68.5 g (0.25 mole) of hexadecyldimethylamine and 42.1 g (0.25 mole) of 2-hydroxy-4-methoxybenzoic acid in 162 g of water and 32 g of isopropanol with 22.1 g (0.5 mole) of ethylene oxide, a degree of quaternization of 93% being achieved.

Example 6

A concentration series of 750, 1,000, 1,500, 2,000 and 5,000 ppm by weight of n-hexadecyldimethyloxy-ethyl-ammonium salicylate ($C_{16}$DE-Sal) from Example 1 in demineralized water was prepared by weighing out the corresponding amounts by weight of 0.75; 0.1; 0.15; 0.2 and 0.5 g of $C_{16}$DE-Sal per 1,000 g of demineralized water. The solutions were heated briefly to 90° C. during the solution process and, after cooling to room temperature (22° C.), were kept at this temperature for 1 week without being stirred.

The drag reduction is then investigated in a turbulence rheometer.[Polymer Letters 9,851 (1971)] by forcing an amount of liquid of 1.5 litres through the measurement tube with the aid of a piston, analogously to a syringe. The movement of the piston is accelerated during the measurement, so that the entire flow curve, as shown in the drawing, is recorded in one measurement. The diameter of the measurement tube is 3 mm, the measurement zone for $\Delta P$ is 300 mm and the run-in zone is 1,200 mm.

The same concentration series of $C_{16}$DE-Sal was measured in this apparatus at 22° C., 40° C., 55° C. and 65° C., after the solutions have first each been kept at corresponding temperatures for 1 week.

Table 1 summarizes the results of all the measurements by showing the $Re_{max}$ and $\alpha_{max}$. The accompanying drawing shows, in a double-logarithmic plot of $\ln\lambda$ against $\ln Re$, the flow curves for the concentrations 750, 1,000 and 2,000 ppm measured in the turbulence rheometer at 40° C.

Example 7

Solutions of $C_{20/22}H_{41/45}N(CH_3)_2CH_2CH_2OH$ salicylate (abbreviated to $C_{20/22}$DE-Sal) (cf. Example 3) in water in concentrations of 1,000, 2,000 and 3,000 ppm by weight were prepared and investigated for drag resistance in a turbulence rheometer at 80° C., as described in Example 6. The following effects were found: for 1,000 ppm: $Re_{max}=5,200\pm520$ and $\alpha_{max}=57\pm3$; for 2,000 ppm: $Re_{max}=7,500\pm750$ and $\alpha_{max}=34\pm2$; and for 3,000 ppm: $Re_{max}=1,040$ and $\alpha_{max}=40\pm3$.

Example 8

Solutions with a concentration of in each case 750 ppm ($1.66\times10^{-3}$ mole/liters) of $C_{16}$DE-Sal were prepared as in Example 6, and were brought to pH values of 3.0; 4.1; 7.9; 9.2 and 11, with HCl for pH values of less than 7 and with NaOH for pH values above 7, and measured in a turbulence rheometer at 40° C. The NaOH and HCl were added before the solutions were heated up to 90° C., and the pH values were determined immediately before the measurement in the turbulence rheometer. As the results in Table 2 show, bringing the pH value to below 4 or above 10 causes a considerable improvement in the effectiveness as a DRA in comparison with pure $C_{16}$DE-Sal solution of the same concentration, as described in Example 6.

Example 9

Different amounts of NaCl together with CTA-Sal, were made up into aqueous solutions, as described in Example 6, in which the concentrations (in moles/liters) of $C_{16}$DE-Sal were in each case 750 ppm ($1.66\times10^{-3}$ moles/liters) and of NaCl were chosen as follows: $5\times10^{-5}$; $1\times10^{-4}$; $1.66\times10^{-3}$; $5\times10^{-3}$; 0.01; 0.05 and 0.1. The results of the investigation for drag reduction at 40° C. in a turbulence rheometer are summarized in Table 3. As can be seen from Table 3, the addition of NaCl up to a 40-fold to 60-fold molar excess improves the effect of $C_{16}$DE-Sal as a DRA.

Example 10

Aqueous solutions containing in each case 750 ppm ($1.66\times10^{-3}$ moles/liter) of $C_{16}$DE-Sal and the following concentrations of $Na_2CO_3$ (in moles/liters): $5\times10^{-5}$; $1\times10^{-4}$; $5\times10^{-4}$; $1.66\times10^{-3}$; $5\times10^{-3}$; 0.01 and 0.05, were prepared as described in Examples 6 and 9. The results of the investigation for drag reduction in a turbulence rheometer at 40° C. are summarized in Table 4. Even the addition of only $5\times10^{-4}$ mole/liter of $Na_2CO_3$ together with an increase in the pH value of the solution to 10.4 clearly improves the effect as a drag reducing agent in comparison with a $1.66\times10^{-3}$ molar solution of $C_{16}$DE-Sal without the addition of a salt.

Example 11

Aqueous solutions containing in each case 750 ppm ($1.66\times10^{-3}$ moles/liters) of $C_{16}$DE-Sal and the following concentrations of $Na_3PO_4$ (in moles/liters): $2\times10^{-5}$; $5\times10^{-5}$; $1\times10^{-4}$; $5\times10^{-4}$; $1.66\times10^{-3}$; $5\times10^{-3}$; 0.01 and 0.05 were prepared as described in Examples 6 and 9. The results of the investigations for drag reduction in a turbulence rheometer at 40° and 55° C. are summarized in Table 5. A clear improvement in the effectiveness as a drag reducing agent compared with a 750 ppm ($1.66\times10^{-3}$ molar) solution of $C_{16}$DE-Sal without additions occurs at $Na_3PO_4$ concentrations in the region of $5\times10^{-3}$ mole/liter.

Example 12

Aqueous solutions containing in each case 750 ppm ($1.66\times10^{-3}$ mole/liter) of $C_{16}$DE-Sal and the following concentrations of $AlCl_3$ (in moles/liters): $2\times10^{-5}$; $5\times10^{-5}$; $1\times10^{-4}$; $5\times10^{-4}$; $1.66\times10^{-3}$ and $5\times10^{-3}$ were prepared as described in Examples 6 and 9. The investigations of the solutions for drag reduction in a turbulence rheometer at 40° C. showed a drag reduction with in each case $Re_{max}=6,500\pm600$ and $\alpha_{max}=54\pm4$ for the $AlCl_3$ concentrations of $2\times10^{-5}$ to $5\times10^{-4}$ mole/liter, and no further drag reduction for $AlCl_3$ concentrations above $5\times10^{-4}$ mole/liter.

Example 13

Aqueous solutions containing in each case 750 ppm ($1.66\times10^{-3}$ mole/liter) of $C_{16}$DE-Sal and the following concentrations of $CaCl_2$ (in mole/liter): $1\times10^{-4}$; $5\times10^{-4}$; $1.66\times10^{-3}$ and 0.01 were prepared as described in Examples 6 and 9. The investigations of the solutions for drag reduction in a turbulence rheometer at 40° C. are summarized in Table 6. As can be seen from Table 6, the addition of $5\times10^{-4}$ mole/liter to 0.01 mole/liter of $CaCl_2$ clearly improves the effectiveness as a DRA in comparison with the electrolyte-free solution.

Example 14

To investigate the drag reduction in a long-term experiment at 60° C., a closed flow apparatus consisting of a 30 liters stock vessel, a centrifugal pump (type: CPK 50-250 from KSB with a mechanical variable feed gear), an inductive flow meter and a pipeline 20 m long with an internal diameter of 29.75 mm was utilized. The pressure drop ΔP was determined, after an associated runin zone, as a measurement zone of 2 m. An immersion heater which electrically heated the liquid in the stock tank was used for thermostatic control. During the long-term experiment, the liquid was continuously pumped from the bottom of the stock vessel and fed back to the stock vessel via the pipeline. For demineralized water at 60° C., the conveying capacity of the pump can be varied from 3 to 15 m³/hour with the mechanical variable speed gear, corresponding to flow rates of 1.25 to 5.6 m/s, or Reynolds' numbers from 78,400 to 351,000 for the pipe diameter of 29.75 mm.

A 4,000 ppm solution of n-hexadecyldimethyloxyethyl-ammonium saclcylate ($C_{16}DE$-Sal), prepared as described in Example 1, was investigated in this apparatus for its stability, with respect to time, as a drag reducing agent at 60° C. The long-term experiment was carried out at a throughput of 13 m³/hour, corresponding to a flow rate of 5.2 m/second and a Reynolds' number of 326,165, over a period of 14 days. Under the above conditions, the same volume of liquid passes the centrifugal pump about 5 times per minute. In spite of the very high sheer stress, a constant drag reduction of 75±4% was found over the entire experimental period of 14 days. No decrease in effectiveness through degradation was to be found.

Example 15

In a first experiment, an aqueous solution containing 5,000 ppm of dodecyldimethyloxyethylammonium salicylate ($C_{12}DE$-Sal), cf. Example 2, was prepared as described in Example 6 and investigated for drag reduction in a turbulence rheometer at 25° C. Drag reduction with $Re_{max}=34,000\pm$ and $\alpha_{max}=37\pm4\%$ was found.

In a second experiment, the same 5,000 ppm solution of $C_{12}DE$-Sal was investigated for drag reduction at 10, 15 and 20° C. in a disk apparatus. In the disk apparatus mentioned, a disk 260 mm in diameter and 7 mm thick rotates in the solution to be investigated. The disk and solution are in a housing, which can be thermostatically controlled, with an internal diameter of 300 mm, the width of the gap between the disk and the bottom plate and the disk and the top plate being in each case 14 mm. The torque M of the disk is measured as a function of the number of revolutions U. The following dimensional parameters can be calculated from the two measurement parameters:

$$\lambda = \text{Coefficient of drag} = \frac{M}{0.5\rho \omega^2 R^5}$$

$$Re = \text{Reynolds' number} = \frac{\omega R^2}{\nu}$$

A double-logarithmic plot of λ against Re then gives comparable flow curves to those shown in FIG. 1 for the turbulence rheometer. The flow curve for water without additives is represented in the turbulent region by $$\lambda = \frac{0.0619}{Re^{0.164}}$$

The drag reduction α is calculated analogously to that for flow through a pipe; however, the value of α is only ½ to ⅔ of the α value which results when the same solution is investigated in a turbulence rheometer. For the disk apparatus described, the change from turbulent to lamina flow takes place at a Reynolds' number of 230,000.

The following drag reductions were found, depending on the temperature, for the aqueous solution containing 5,000 ppm of $C_{12}DE$-Sal, in each case at Re=2,400,000: for 10° C.: α=46.7%; for 15° C.: α=45.2%; for 20° C.: α=33.5%. The results show that the turbulence rheometer and disk apparatus are equally suitable for testing for drag reduction.

Example 16

Solutions containing 2,500 to 5,000 ppm of dodecyldimethyloxyethylammonium salicylate ($C_{12}DE$-Sal) were prepared as described in Example 6. A mixture of 90% by weight of demineralized water and 10% by weight of ethylene glycol was used as the solvent. These solutions were investigated for drag reduction in the disk apparatus at temperatures of −3° C. to 10° C., as described in Example 9. As the summary of the results in Table 7 shows, the DR action is retained even when ethylene glycol is admixed and at below 0° C. Of the compounds claimed according to the invention, $C_{12}DE$-Sal is therefore particularly suitable for use in cooling circulations in which temperatures below 0° C. can be achieved by means of additives such as polyalcohols.

Example 17

A concentration series of 750, 1,500 and 3,000 ppm by weight of n-hexadecyldimethyloxyethylammonium-4-methoxy salicylate ($C_{16}DE$-4-methoxysalicylate), cf. Example 5, in demineralized water was prepared as described in Example 6 and investigated for drag reduction in a turbulence rheometer at 40° C. A 10,000 ppm by weight solution of n-hexadecyldimethyloxyethylammonium caprylate ($C_{16}DE$-caprylate), cf. Example 4, was treated analogously. Table 8 summarizes the results.

Example 18

Aqueous solutions of various n-hexadecyldimethyloxyethylammonium salts ($C_{16}DE$-salt), such as $C_{16}DE$-1-nonate, $C_{16}DE$-2-hydroxy-3-naphthoate and $C_{16}$-heptane-1-sulfonate, were prepared by weighing out the salts $C_{16}DE$-Cl and Na 1-nonate, or Na 2-hydroxy-3-naphthoate, or Na 1-heptanesulfonate in a molar ratio of 1:1, and the solutions were pretreated as described in Example 6. Table 9 summarizes the measurement results obtained for the various aqueous solutions of different concentrations.

TABLE 1

| T/°C. | Concentration/ppm | $Re_{max}$ | $\alpha_{max}$ |
|---|---|---|---|
| 22 | 750 | 3600 ± 360 | 37 ± 3 |
| " | 1000 | 4900 ± 490 | 50 ± 3 |
| " | 1500 | 6800 ± 680 | 51 ± 3 |
| " | 2000 | 10300 ± 1030 | 58 ± 3 |
| 40 | 300 | 3600 ± 360 | 07 ± 3 |
| " | 500 | 5000 ± 500 | 48 ± 3 |
| " | 750 | 6400 ± 640 | 53 ± 3 |
| " | 1000 | 8200 ± 820 | 56 ± 3 |
| " | 1500 | 9100 ± 910 | 56 ± 3 |
| " | 2000 | 13250 ± 1300 | 62 ± 3 |
| " | 5000 | 18400 ± 1800 | 62 ± 3 |
| 55 | 1000 | 6000 ± 600 | 55 ± 3 |
| " | 1500 | 8900 ± 890 | 64 ± 3 |
| " | 2000 | 12900 ± 1300 | 67 ± 3 |
| " | 5000 | 28100 ± 2800 | 70 ± 3 |
| 65 | 5000 | 12900 ± 1300 | 57 ± 3 |

TABLE 2

$C_{16}De$—Sal concentration: 750 ppm, measurement temperature 22° C.

| Concentration/ppm | pH value | $Re_{max}$ | $\alpha_{max}$ |
|---|---|---|---|
| 750 | 3.0 | 9700 ± 1000 | 56 ± 3 |
| 750 | 4.1 | 7100 ± 700 | 54 ± 3 |
| 750 | 7.9 | 6300 ± 600 | 53 ± 3 |
| 750 | 9.2 | 6900 ± 700 | 54 ± 3 |
| 750 | 11.0 | 11700 ± 1200 | 65 ± 3 |

TABLE 3

$C_{16}DE$—Sal concentration: 750 ppm, measurement temperature 40° C.

| NaCl concentration mole/l | $Re_{max}$ | $\alpha_{max}$ |
|---|---|---|
| $5 \times 10^{-5}$ | 7000 ± 700 | 56 ± 3 |
| $1 \times 10^{-4}$ | 7200 ± 700 | 57 ± 3 |
| $5 \times 10^{-4}$ | 9400 ± 900 | 57 ± 3 |
| $1.66 \times 10^{-3}$ | 13200 ± 1300 | 64 ± 3 |
| $5 \times 10^{-3}$ | 16100 ± 1600 | 67 ± 3 |
| 0.01 | 16100 ± 1600 | 67 ± 3 |
| 0.05 | 13000 ± 1300 | 66 ± 3 |
| 0.1 | 9600 ± 1000 | 60 ± 3 |

TABLE 4

$C_{16}DE$—Sal concentration: 750 ppm, measurement temperature 40° C.

| NaCO₃ concentration mole/l | pH value | $Re_{max}$ | $\alpha_{max}$ |
|---|---|---|---|
| $5 \times 10^{-5}$ | 8.8 | 6500 ± 600 | 54 ± 3 |
| $1 \times 10^{-4}$ | 8.8 | 7700 ± 800 | 54 ± 3 |
| $5 \times 10^{-4}$ | 10.4 | 15700 ± 1600 | 66 ± 3 |
| $1 \times 66\, 10^{-4}$ | 11.0 | 16500 ± 1600 | 66 ± 3 |
| $5 \times 10^{-3}$ | 11.3 | 13600 ± 1400 | 67 ± 3 |
| 0.01 | 11.4 | 11700 ± 1200 | 65 ± 3 |

TABLE 5

| T/°C. | Na₃PO₄ concentration mole/l | pH value | $Re_{max}$ | $\alpha_{max}$ |
|---|---|---|---|---|
| 40 | $2 \times 10^{-5}$ | 8.6 | 8100 ± 800 | 57 ± 3 |
| " | $5 \times 10^{-5}$ | 8.6 | 10200 ± 1000 | 57 ± 3 |
| " | $1 \times 10^{-4}$ | 9.0 | 14600 ± 1500 | 69 ± 3 |
| " | $5 \times 10^{-4}$ | 9.9 | 16600 ± 1700 | 66 ± 3 |
| " | $1.66 \times 10^{-3}$ | 11.2 | 15100 ± 1500 | 67 ± 3 |
| " | $5 \times 10^{-3}$ | 11.8 | 9700 ± 1000 | 69 ± 3 |
| " | 0.01 | 12.1 | 7200 ± 7000 | 57 ± 3 |
| " | 0.1 | 12.5 | no effect | — |
| 55 | $5 \times 10^{-5}$ | " | 4800 ± 500 | 35 ± 2 |
| " | $1 \times 10^{-4}$ | " | 11200 ± 1100 | 68 ± 3 |
| " | $5 \times 10^{-4}$ | " | 19300 ± 1900 | 72 ± 3 |
| " | $1.66 \times 10^{-4}$ | " | no effect | — |

TABLE 6

$C_{16}DE$—Sal concentration: 750 ppm, measurement temperature 40° C.

| CaCl₂ concentration mole/l | $Re_{max}$ | $\alpha_{max}$ |
|---|---|---|
| $1 \times 10^{-4}$ | 7500 ± 750 | 57 ± 3 |
| $5 \times 10^{-4}$ | 10400 ± 1000 | 62 ± 3 |
| $1.66 \times 10^{-3}$ | 13300 ± 1300 | 70 ± 3 |
| 0.01 | 13700 ± 1400 | 69 ± 3 |

TABLE 7

$C_{12}DE$—Sal in water/ethylene glycol 90/10

| T/°C. | Concentration/ppm | Re | $\alpha$ |
|---|---|---|---|
| 0 | 5000 | 1080000 | 37,8 ± 2 |
| −3.0 | 5000 | 1080000 | 32 ± 1 |
| −1.0 | 2500 | 1090000 | 32,5 ± 2 |

TABLE 7-continued $C_{12}DE$—Sal in water/ethylene glycol 90/10

| T/°C. | Concentration/ppm | Re | $\alpha$ |
|---|---|---|---|
| +5.0 | 2500 | 1090000 | 31,0 ± 2 |
| +10.0 | 2500 | 1090000 | 4,8 ± 1 |

TABLE 8

Measurement temperature 40° C.

| Substance | Concentration/ppm | $Re_{max}$ | $\alpha_{max}$ |
|---|---|---|---|
| $C_{16}DE$—4-methoxy-salicylate | 750 | 5000 ± 500 | 51 ± 3 |
|  | 1500 | 7900 ± 800 | 61 ± 3 |
|  | 3000 | 10200 ± 1000 | 62 ± 3 |
| $C_{16}DE$—caprylate | 10000 | 5300 ± 500 | 47 ± 3 |

TABLE 9

| Substance | Temperature °C. | Concentration ppm | $Re_{max}$ | $\alpha_{max}$ |
|---|---|---|---|---|
| $C_{16}DE$—1-nonate | 25 | 3000 | 13200 ± 1300 | 43 ± 3 |
| " | 25 | 5000 | 31500 ± 3200 | 73 ± 4 |
| $C_{16}DE$—2-oxi-3-naphthoate | 60 | 750 | 24200 ± 2400 | 72 ± 4 |
|  | 60 | 1500 | 32800 ± 3300 | 72 ± 4 |
|  | 85 | 2000 | 31200 ± 3100 | 73 ± 4 |
| $C_{16}DE$—1-heptane-sulfonate | 40 | 5000 | 5000 ± 500 | 40 ± 3 |

We claim:

1. A quaternary ammonium compound of the formula

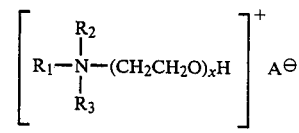

in which $R_1$ denotes an alkyl or alkenyl radical with 12 to 22 C atoms; $R_2$ and $R_3$ are identical or different and denote an alkyl radical with 1 to 4 C atoms; x denotes an integral or non-integral number from 1 to 3; and $A^\ominus$ denotes a straight-chain $C_6$–$C_9$-alkyl-sulfonate or $C_6$–$C_9$-alkenylsulfonate anion, wherein the sum of the carbon atoms in $R_1$ and in the sulfonate anion should be at least 21, a straight-chain $C_6$–$C_9$-alkylcarboxylate or $C_6$–$C_9$-alkenylcarboxylate anion, wherein the sum of the carbon atoms in $R_1$ and in the carboxylate anion should be at least 23, the salicylate anion or an anion of the formulae

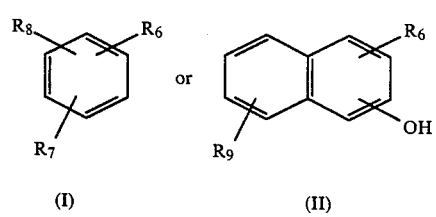

(I)   (II)

in which $R_6$ denotes —COO⁻ or —SO₃⁻, $R_7$ denotes hydrogen, hydroxyl in position 2 or 3 relative to $R_6$, or NO₂, fluorine, chlorine, bromine or iodine in position 3 relative to $R_6$, $R_8$ denotes $C_1$–$C_5$-alkyl, $C_2$–$C_5$-alkenyl or $C_1$–$C_5$-alkoxy in position 3, 4 or 5 relative to $R_6$, and $R_9$ denotes hydrogen or methyl, except that, in formula (I), $R_7$ is not hydrogen if $R_8$ is methyl and $R_6$ is —SO⁻₃.

2. A quaternary ammonium compound as claimed in claim 1, wherein said $A^\ominus$ is an anion of the formula

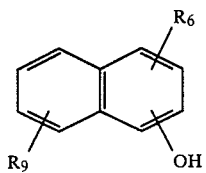

$R_6$ being $-COO^\ominus$ or $-SO_3^\ominus$, and $R_9$ being hydrogen or methyl.

3. A quaternary ammonium compound as claimed in claim 1, wherein said $A^\ominus$ is the salicylate anion or an anion of the formula

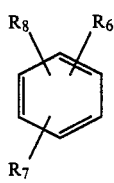

in which $R_6$ denotes $-COO^\ominus$ or $-SO_3^\ominus$, $R_7$ denotes hydrogen or hydroxy in position 2 or 3 relative to $R_6$, or $NO_2$, fluorine, chlorine, bromine, or iodine in position 3 relative to $R_6$; $R_8$ denotes $C_1-C_5$ alkyl, except when $R_7$ is hydrogen, in which case $R_8$ is not methyl, or $R_8$ is $C_2-C_5$ alkenyl or $C_1-C_5$ alkoxy in position 3, 4 or 5 relative to $R_6$.

4. A compound of the formula

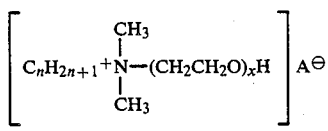

in which x denotes an integral or non-integral number from 1 to 1.5, n denotes a number from 12 to 24 and $A^\ominus$ denotes an anion from the group (a) $C_6H_{13}SO_3^-$ for the case where $n=20-24$,
(b) $C_7H_{15}SO_3^-$ for the case where $n=14-22$,
(c) $C_8H_{17}SO_3^-$ for the case where $n=14-20$,
(d) 2-phenylsulfonate, m-halogenobenzoate or salicylate,
(e) an anion of the formula

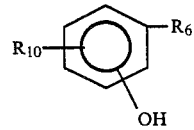

where $R_6=SO_3^-$ or $COO^-$ and $R_{10}=C_1-C_4$-alkyl or $C_1-C_4$-alkoxy, (f) 2-hydroxy-1-naphthoate, 3-(or 4)-hydroxy-2-naphthoate and the corresponding naphtholsulfonic acid anions, the tosylate ion being excluded.

5. A compound as claimed in claim 4, wherein $A^-$ is a salicylate anion.

6. A quarternary ammonium compound of the formula

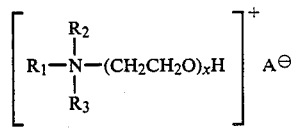

in which $R_1$ denotes an alkyl or alkenyl radical with 12 to 22 C atoms; $R_2$ and $R_3$ are identical or different and denote an alkyl radical with 1 to 4 C atoms; x denotes an integral or non-integral number from 1 to 3; and $A^-$ denotes an anion of the formulae

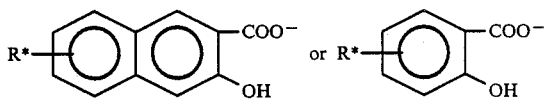

wherein $R^*$ is hydrogen, $C_1-C_5$-alkoxy.

7. A compound as claimed in claim 4, where $R_6$ is $COO^\ominus$ and $R_{10}$ is in position 4 or 5 relative to $R_6$ and with OH in position 2 or 3 relative to the carboxyl group.

* * * * *